United States Patent [19]

Bird

[11] 4,148,312
[45] Apr. 10, 1979

[54] COMBINATION ANESTHESIA AND INTENSIVE CARE APPARATUS

[75] Inventor: Forrest M. Bird, Palm Springs, Calif.

[73] Assignee: Minnesota Mining and Manufacturing Company, St. Paul, Minn.

[21] Appl. No.: 730,727

[22] Filed: Oct. 8, 1976

[51] Int. Cl.² ............................................ A61M 16/00
[52] U.S. Cl. ................................. 128/145.6; 128/188
[58] Field of Search ............... 128/145.6, 145.8, 145.5, 128/188, 142.2, 377; 32/22; 128/203, 2 T, 2 V, 303.1; 312/209

[56] References Cited

U.S. PATENT DOCUMENTS

| 2,023,563 | 12/1935 | Willison | 128/377 |
| 3,081,542 | 3/1963 | Shefrey | 32/22 R |
| 3,156,238 | 11/1964 | Bird et al. | 128/145.6 |
| 3,191,596 | 6/1965 | Bird et al. | 128/145.5 |
| 3,333,584 | 8/1967 | Andreasen et al. | 128/145.5 |
| 3,386,766 | 6/1968 | Gorelick | 32/22 R |
| 3,621,842 | 11/1971 | Manley | 128/145.6 |
| 4,020,834 | 5/1977 | Bird | 128/145.6 |

FOREIGN PATENT DOCUMENTS 2452640  7/1975  Fed. Rep. of Germany ........ 128/145.6

OTHER PUBLICATIONS

Ohio Chemical Products, Oct. 4, 1963, p. 7.

Primary Examiner—Henry J. Recla

[57] ABSTRACT

Combination anesthesia and intensive care unit having an anesthesia apparatus in the form of an analgesia generator and a anesthesia respirator and with a vaporizer and $CO_2$ absorber mounted thereon. A removable chair assembly is connected to the stand and is to be used by the anesthesiologist in operating the anesthesia apparatus for intensive care. A respirator and a patient breathing monitoring apparatus are also mounted upon the stand. When used as an intensive care unit, the chair assembly can be disconnected from the stand.

4 Claims, 4 Drawing Figures

COMBINATION ANESTHESIA AND INTENSIVE CARE APPARATUS

BACKGROUND OF THE INVENTION

Anesthesia apparatus has heretofore been provided. However, such anesthesia apparatus has been very complicated and expensive to fabricate. In addition, such anesthesia apparatus has not been designed to minimize fatigue to the anthesiologist utilizing the same. In addition, such apparatus in the past has been limited to a single use. There is therefore a need for a new and improved anesthesia apparatus.

SUMMARY OF THE INVENTION AND OBJECTS

The combination anesthesia and intensive care unit consists of the stand with a source of anesthesia gases to be connected thereto. Anesthesia apparatus in the form of a $CO_2$ absorber, a vaporizer, an analgesic generator and an anesthesia respirator are mounted upon the stand. A patient adapter is provided. A bellows is provided which has its interior connected to the patient adapter. A canister is provided for the bellows. The anesthesia gases are supplied from the analgesic unit to the interior of the bellows. The respirator is provided with a controller for supplying gases to the interior of the canister to compress the bellows during the inhalation phase. Exhalation valve means is connected to the interior of the canister for the discharge of gas from the interior of the canister during the exhalation phase. A chair assembly is removably secured to the stand and for use by the anesthesiologist in operating the anesthesia apparatus. For intensive care applications, a respirator is carried by the stand. In addition, a patient breathing monitoring apparatus is also provided to monitor the operation of the respirator.

In general, it is an object of the present invention to provide a combination anesthesia and intensive care unit which can be utilized for both anesthesia and intensive care in medical applications.

Another object of the invention is to provide a unit of the above character which has a chair secured thereto for use by the anesthesiologist for operation of the apparatus.

Another object of the invention is to provide a unit of the above character which has an anesthesia apparatus having capabilities for supplying a constant airway pressure against which the patient must exhale.

Another object of the invention is to provide a unit of the above character in which the anesthesia apparatus is provided with flow acceleration during the inspiratory phase.

Another object of the invention is to provide a unit of the above character in which anesthesia gases which are discharged from the system are scavenged.

Another object of the invention is to provide a unit of the above character in which the chair can be readily removed.

Another object of the invention is to provide a unit of the above character which is relatively inexpensive and which is very versatile.

Additional objects and features of the invention will appear from the following description in which the preferred embodiment is set forth in detail in conjunction with the accompanying drawing.

DESCRIPTION OF THE PREFERRED EMBODIMENT

Figure 1:
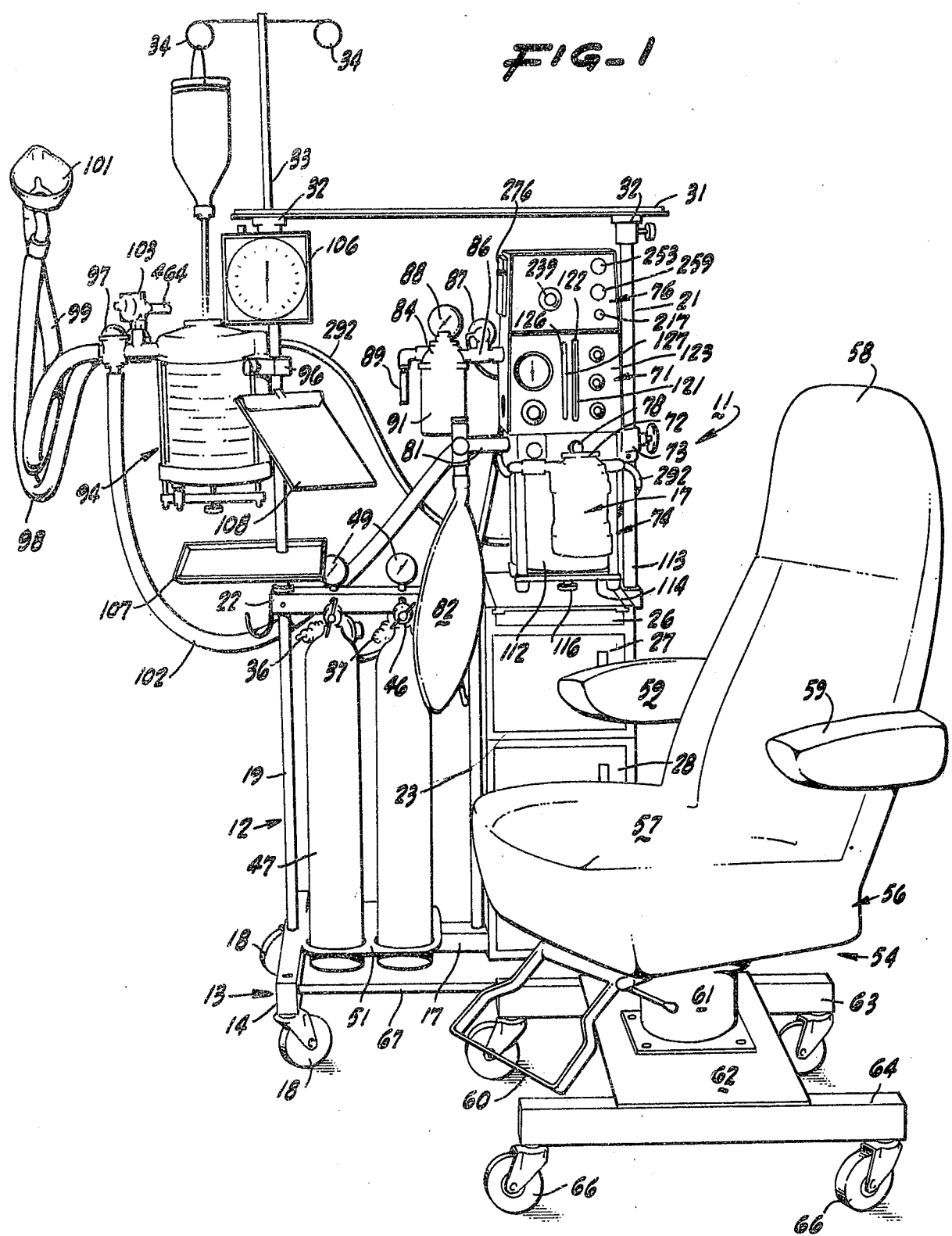
FIG. 1 is a front elevational perspective view of an anesthesia apparatus forming a part of the combination anesthesia intensive care unit comprising the present invention.
Figure 2:
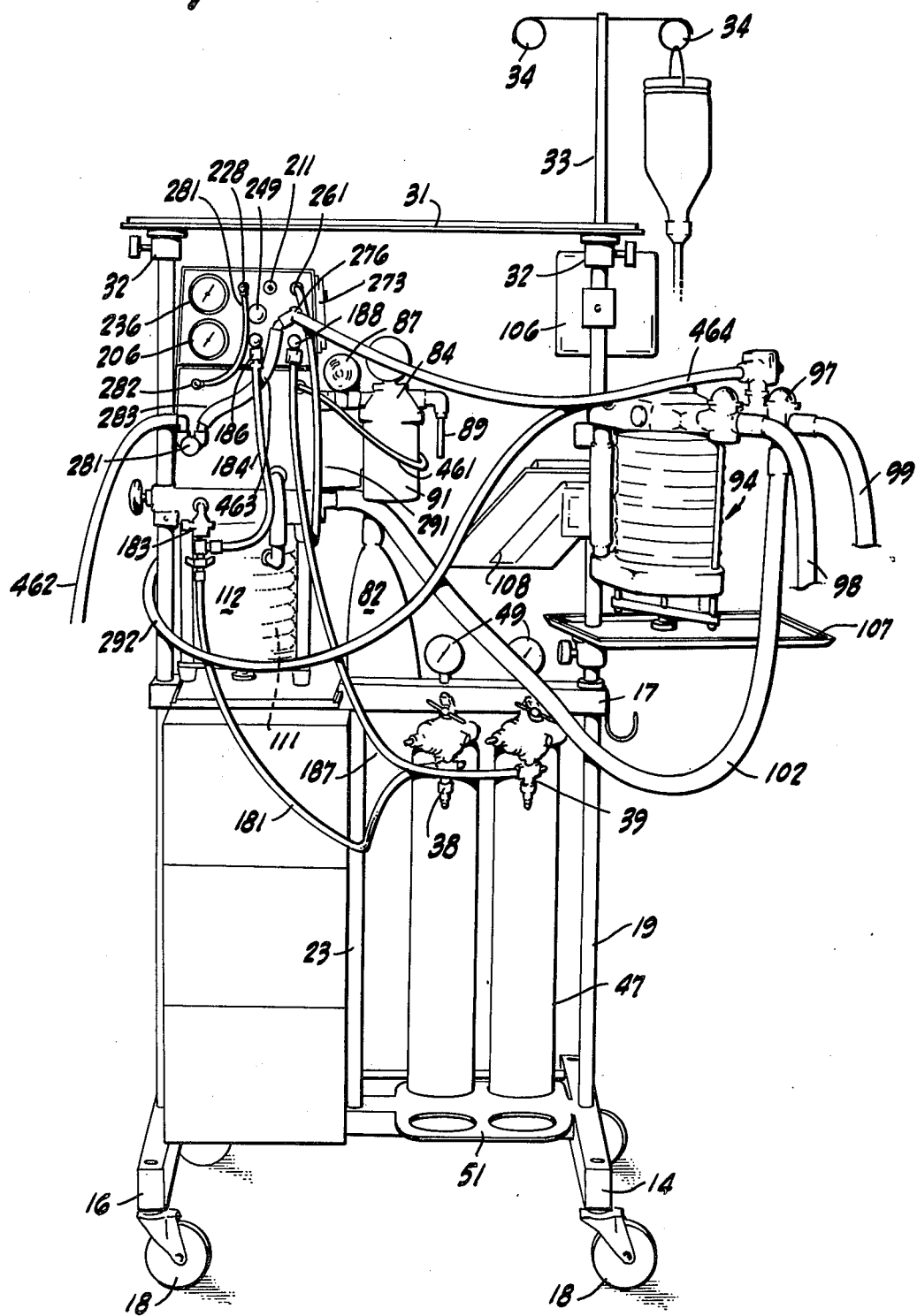
FIG. 2 is rear elevational perspective view of the apparatus shown in FIG. 1 with the chair assembly removed.

The combination anesthesia and intensive care apparatus 11 consists of a large stand 12. The stand 12 is provided with a base 13 formed of a pair of spaced parallel members 14 and 16 which are joined together by a centrally disposed member 17 secured thereto by a suitable means such as screws (not shown). Castered wheels 18 are carried by opposite ends of the members 14 and 16 so that the base can be readily moved from one location to another. The stand 12 also includes a pair of vertical support rods 19 and 21 which are mounted in the members 14 and 16, equidistant between the ends are the same and extend upwardly in a vertical direction. A cross member 22 is slidably mounted upon the support rods 19 and 21 as secured thereto by suitable means such as screws (not shown). An intermediate support rod 23 is provided between the cross member 22 and the cross member 17 and secured between the two members to provide additional support.

A metal cabinet 26 is supported upon the lower cross member 17 and is disposed between the rod 21 and the rod 23. The cabinet 26 is provided with the three drawers 27 each having a handle 28 to facilitate opening of the drawer. The stand 12 also includes an upper shelf 31 by which is secured to the upper ends of the rods 19 and 21 by fittings 32 secured to the shelf and secured to the upper ends of rods 19 and 21. An I.V. pole 33 is mounted in the rod 19 and carries hangers 34 for I.V. bottles.

Means is provided on the stand 12 for receiving source gas and consists of a pair of regulators 36 and 37 of a conventional type which are secured in spaced apart positions on the lower part of the cross member 22. The outlets of the regulators are provided with cross-type fittings 38 and 39. One leg of each of the fittings is adapted to be connected to a conventional source of supply such as can be found in hospitals which is already at the desired pressure as for example 50 psi. The two types of gases which are conventionally used with the apparatus 11 would be oxygen and nitrous oxide.

The other leg of each of the tee shaped fittings is secured to other apparatus mounted in the stand as hereinafter described. The inlets of the regulators 36 and 37 are connected to passages (not shown) provided in the cross member 22 which are in communication with brackets 46 mounted upon the cross member 22. The brackets 26 are adapted to receive the upper ends of gas bottles 47 which are carried by the stand 12. As can be seen, two oxygen bottles and two nitrous oxide bottles are provided to assure an adequate emergency supply. The gas in these bottles is reduced to the desired pressure, as for example 50 psi by the regulators 36 and 37. Gauges 49 carried by the cross member 22 give a reading of the pressure of the gases in the bottles. A separating plate 51 is mounted upon the bottom cross member 17 and is provided with holes (not shown) which receive the lower extremities of the bottles 47 to prevent them from bumping into each other as the stand is moved.

A chair assembly 54 is associated with the apparatus which is adapted to be used by the anesthesiologist operating the apparatus. The chair assembly 54 also includes a pedestal 61 upon which the chair 56 is mounted. The pedestal is carried by plate 62 that extends across and is secured to a pair of spaced parallel members 63 and 64. A castered wheel 66 is provided on the opposite ends of the members 63 and 64 to provide a four-point support for the chair.

Means is provided for securing the chair assembly 54 to the stand 12 so that it can be moved with the stand and its position can be adjusted with respect to the stand. For this purpose, the stand has been provided with a rod 67 extending between the members 14 and 16 which is adapted to be engaged by a pair of clamps secured to the member 63 of the chair assembly. The clamps are such that when they are loosened, the chair assembly 54 can be moved longitudinally with respect to the axis of the rod 67. The chair is swivel mounted upon the pedestal 61 so that the anesthesiologist can shift his position with respect to the apparatus carried by the stand. The chair is provided with a U-shaped foot rest 60 which can be utilized by the anesthesiologist.

The equipment which is mounted on the stand 12 and which forms a part of the apparatus for administering anesthesia includes an anesthesia respirator 71 which is mounted upon the center body 72. The center body 72 is provided with a bracket 73 which can be adjusted to be secured vertically above the vertical rod 21. A bellows assembly 74 is secured to the lower portion of the center body 72 and is carried thereby. An analgesia generator 76 is mounted on top of the anesthesia respirator 71. A vaporizer 77 of a conventional type such as Fluotec 3 manufactured by Cyprane, Ltd. of England using a gas such as halothane is secured to the front of the center body by suitable means such as thumbscrew 78. A tee-shaped fitting 81 is also mounted on the center body 72 and has a flexible bag 82 depending therefrom.

A suction unit 84 of conventional type is mounted on one end of a tee 86 which is mounted upon the anesthesia respirator 71. One leg of the tee is connected to an air inlet filter 87. A gauge 88 is provided for reading the vacuum which is present within the suction unit 84. The suction unit 84 is provided with an outlet tube 89 which is adapted to be connected to the patient. The suction unit 84 is provided with a removable receptable 91 for receiving the liquids which are picked up from the patient by the suction unit.

A conventional $CO_2$ absorber 94 such as one manufactured by Ohio Medical Products is secured by bracket 96 to the vertical rod 19. The $CO_2$ absorber 94 is provided with a pair of check valves 97 which are connected to large tubes 98 and 99 connected to a face mask 101 adapted to be placed over the face of the patient. The $CO_2$ absorber 94 is provided with an anesthesia gas through a large tube 102 which is connected into an outlet provided in the center body 72. The $CO_2$ absorber also includes a relief valve 103 the outlet of which is connected to one of the scavenging ports provided on the anesthesia respirator 71 as hereinafter described.

Other equipment associated with the apparatus includes a blood pressure monitor 106 which is mounted on the rod 19. It also includes a tray 107 which is provided with a bracket (not shown) for mounting the tray in adjustable positions on the vertical rod 19. It also includes a clip board 108 that is secured in adjustable positions on the vertical rod 19 by a clamp (not shown).

The center body 72 generally of the type disclosed in U.S. Pat. No. 3,156,238. The bellows assembly 74 is very similar to the bellows assembly shown in U.S. Pat. No. 3,156,238 and as described therein includes a corrugated bellows 111 which is generally cylindrical in shape with an open upper end in engagement with the body 72 clamped thereto by an open ended cylindrical bellows container 112. The bellows container 112 is clamped to the body 72 by the use of four depending rods 113 secured to the body, a pair of clamping bars 114 are pivotally carried by two of the rods whereas the other ends are adapted to hook about the other rods 113 to provide support for screws 116 threaded into the bars 114 and having their upper extremities engage the bottom of the bellows container 112. As described in said U.S. Pat. No. 3,156,238, the center body 72 is provided with a passage (not shown) which is in communication with the interior of the bellows 111.

As also described in said U.S. Pat. No. 3,156,238, the interior of the bellows 111 is in communication with a chamber (not shown) in the center body 72 through a passage in the center body 72. Three outlet ports are provided in the center body 72 which are in communication with the chamber in the center body 72. The first port receives the fitting 81 carrying the bag 82. The second has a pressure relief valve 117 mounted therein. A shuttle valve member (not shown) which is provided with a knob 118 is slidably mounted in the center body 72 and is movable between two positions. In the innermost position, automatic operation of the anesthesia respirator 71 takes place as hereinafter described. When the shuttle valve member is pulled out, the anesthesia respirator 71 is converted to manual operation under control of the bag 82. A tube (not shown) is disposed within the interior of the bellows and is slidably mounted in the center body 72. The tube has openings in the lower end which open into the interior of the bellows. The tube has a button on its lower end which engages the bottom of the bellows. When the bellows 111 is raised as hereinafter described the button causes the tube to follow the movement of the bellows 111.

The upper end of the tube slidably mounted in the center body 72 and is open but has mounted thereon a cage assembly which has therein a valve assembly which can be called a scavenging plunger movable between open and closed positions with respect to the upper end of the tube. The valve assembly is provided with an upwardly extending valve engaging member which is adapted to be engaged by a crosshead slidably mounted upon a pair of rods carried by the center body. A forwardly extending rod is carried by the body and is provided with a pointer 121 associated with a scale 122 provided on the front panel 123 of the anesthesia respirator 71 to give an indication of the amount of gas being inhaled by the patient. As for example, it can be calibrated from zero to 2,000 c.c.

A stop plate is carried by the cross member and is adapted to engage an upward movable stop. That removable stop carries a thumb screw 126 that serves as a mechanical stop knob which travels in a slot 127 provided in the front panel 123. By adjustment of the thumb screw, the movable stop can be set in the desired position. Where full flow is desired, the movable stop will be at the top end of the slot 127. If a reduced volume is desired, the thumb screw 126 will be loosened and the movable stop adjusted to the desired lowered position. The stop plate is also adapted to engage an operating lever 131 of a refill control valve assembly 132 (see FIG. 4 of the ventilator).

The fitting 38 which is connected to the regulator associated with the oxygen bottles 47 is connected by a tube 181 to a fitting assembly 183 carried by the center body 72. The fitting assembly 183 is connected by tube 184 to an inlet fitting 186 carried by the rear side of the analgesic generator 76. Similarly, the cross member 39 which is connected to the nitrous oxide supply is connected by a tube 187 to nitrous oxide inlet fitting 188 also carried by the rear side of the analgesic generator 76.

Figure 3:
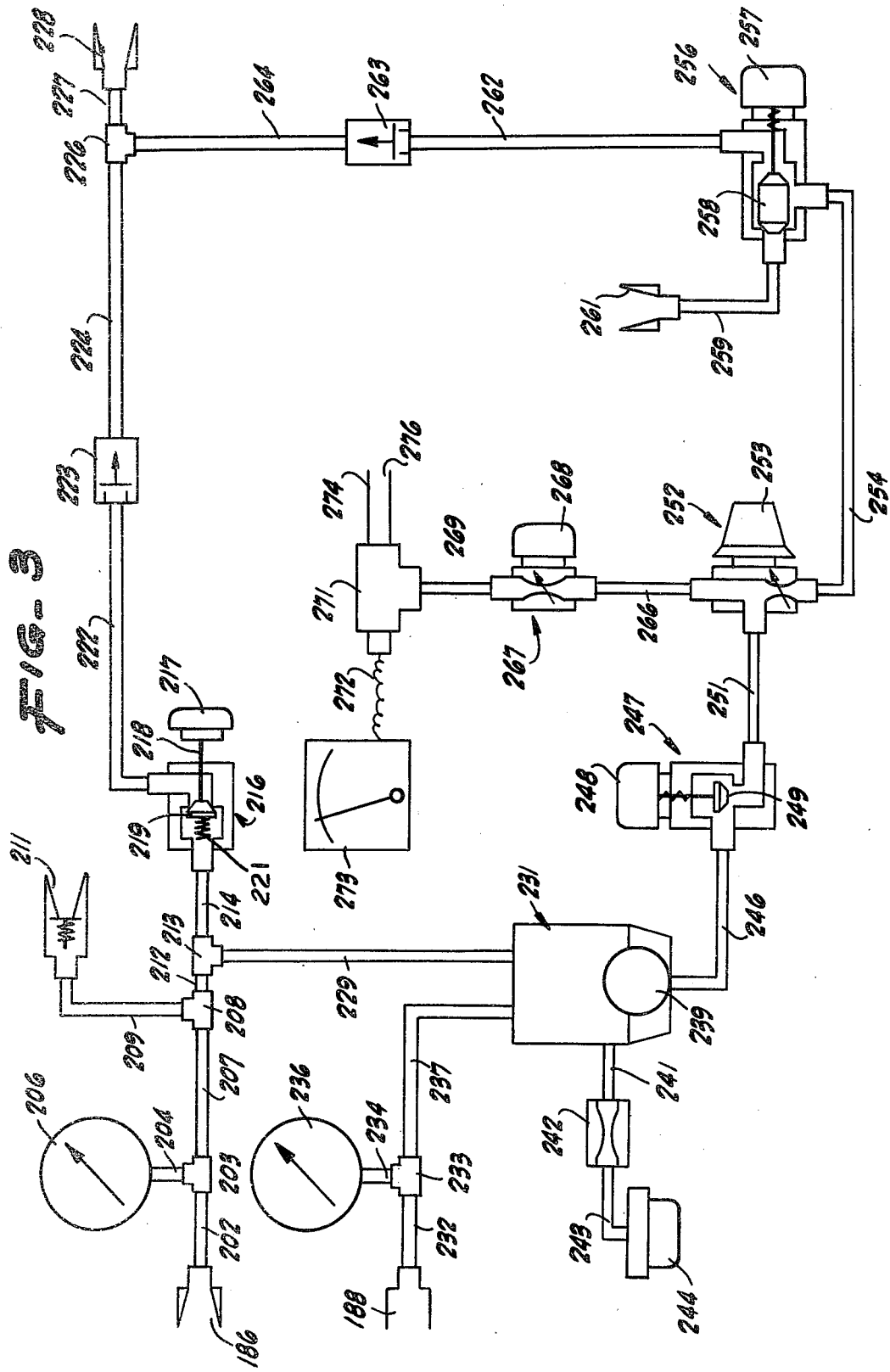
FIG. 3 is a schematic flow of the analgesia generator shown in FIG. 1.

By examining the schematic diagram shown in FIG. 3 it can be seen that the oxygen inlet fitting 186 is connected by a tube 202 to a tee 203. One leg of the tee 203 is connected by a tube 204 to an oxygen pressure gauge 206. A tube 207 connects the tee 203 to a tee 208. The tee 208 is connected by a tube 209 to an aspirator power socket 211. Another leg of the tee 208 is connected by a tube 212 to a tee 213. The tee 213 is connected by a tube 214 to the inlet of an oxygen flush valve 216. The flush valve 216 is provided with a knob 217 carried by a stem 218 of the valve member 219. A spring 221 urges the valve member 219 into a position in which it normally occludes the passage of gas from the tube 214 through a tube 222 connected to the outlet of the flush valve 216. The tube 222 is connected to a check valve 223 which is connected by a tube 224 to a tee 226. Another leg of the tee 226 is connected by a tube 227 to a circle flow outlet fitting 228. Another leg of the tee 213 is connected by a tube 229 to one of the inlets of an oxygen nitrous oxide blender 231.

Nitrous oxide fitting 188 is connected by tube 232 to a tee 233. One leg of the tee 233 is connected by a tube 234 to a nitrous oxide pressure gauge 236. Another leg of the tee 233 is connected by tube 237 to the other inlet of the oxygen nitrous oxide blender 231.

The blender 231 is provided with a control knob 239 on the front side of the analgesia generator 71 which can be utilized to control the ratio of nitrous oxide to oxygen. The blender 231 is connected by a tube 241 to an alarm orifice 242. The alarm orifice 242 is connected by a tube 243 to an alarm device 244 of a conventional type which is mounted on the rear side of the analgesia generator 76.

The output from the blender 231 is connected by tube 246 to a rotary master on/off switch 247. The switch 247 is provided with a control knob 248 which by rotary motion is adapted to position a valve member 249 to control the flow of gas from the tube 246 to a tube 251 connected to the outlet of the master on/off switch 247. The tube 251 is connected to a flow valve assembly 252 of the needle valve type which is provided with a control knob 253. The flow valve assembly 252 is adapted to control the flow of gas from the tube 251 into a tube 254 connected to the outlet of the flow valve assembly 252 to control the rate of flow liters per minute. The tube 254 is connected to the inlet of a rotary vaporizer in/out selector switch assembly 256. The selector switch 256 is provided with a control knob 257 and is adapted to control the position of a valve member 258 to control the flow of gas from the tube 254 to the tube 259. The tube 259 is connected to vaporizer flow outlet fitting 261. The selector switch 256 is provided with two outlets and as can be seen, the valve member 258 is adapted to control the flow of gas from the inlet connected to the tube 254 through either of the two outlets. As pointed out previously, one of the outlets is connected to the tube 259. The other of the outlets is connected by tube 262 to a check valve 263. The check valve is connected by tube 264 into the tee 226 which is in communication with the circle flow outlet 228.

The manifold provided for the needle valve assembly 252 is connected by tube 266 which is in communication with the tube 251 to an adjustable orifice 267 which is provided with a control knob 268. The orifice 267 is connected by a tube 269 to an oxygen analyzer probe 271 of a conventional type such as a Model 300D supplied by Teledyne Analytical Instruments. The probe 271 is connected by an electrical cable 272 to a meter 273 which gives an output reading in percent oxygen. The gas passing into the probe 271 is supplied by a tube 274 to a scavenging outlet 276 provided on the analgesia generator 276.

The circle flow outlet 228 of the analgesia generator is connected by a tube 281 to a circle flow inlet fitting 282 provided on the anesthesia respirator 271. The scavenging flow outlet fitting 276 is connected by a tube 283 to a scavenger fitting 284 also provided on the anesthesia respirator 71.

The vaporizer outlet 261 is connected by a tube 291 to the inlet of the vaporizer 77. The outlet of vaporizer 77 is connected by a tube 292 to the inlet of the $CO_2$ absorber 94.

Figure 4:
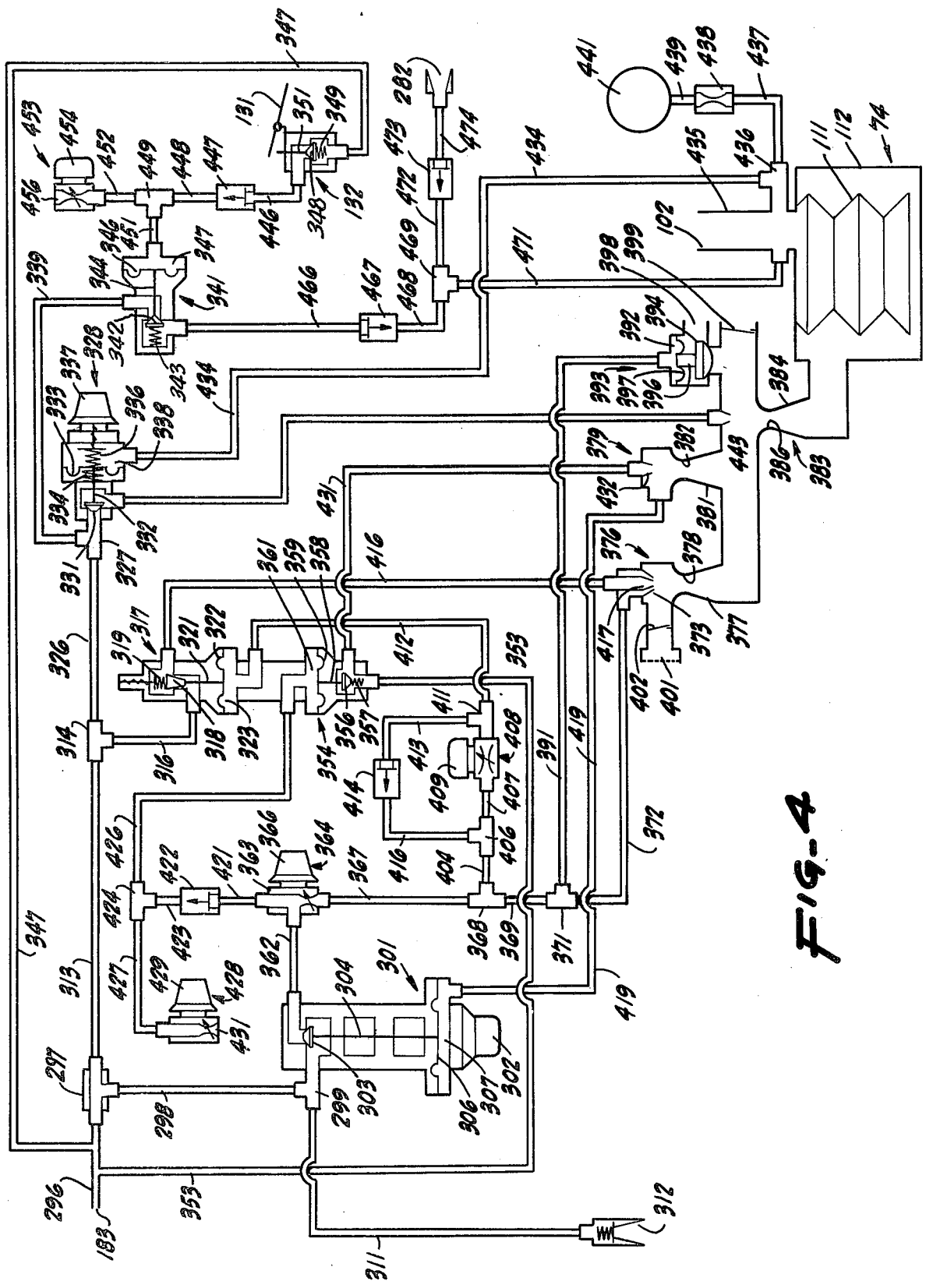
FIG. 4 is a schematic flow diagram of the respirator shown in FIG. 1.

As shown in FIG. 4, oxygen from the fitting 183 is supplied to a tube 296 which is connected to the inlet of a manifold 297. One leg of the manifold is connected by a tube 298 to a tee 299 provided on a sequencing servo assembly 301. The sequencing servo assembly 301 is a conventional type such as described in U.S. Pat. No. 3,753,436, and is provided with control knob 302 which is utilized for adjustably positioning the opening and closing of a valve member 303 carried by a valve stem 304. The valve stem 304 is carried by a diaphragm 306. The sequencing servo assembly is provided with a chamber 307 which is provided on one side of the diaphragm 306. The valve member 303 is movable between open and closed positions to control the flow of gas from inlet 299 of the sequencing servo assembly 301.

Source gas is supplied from another leg of the tee 299 through a tube 311 to an aspirator socket 312. Source gas is also supplied from the manifold 297 through a tube 313 to a tee 314. One leg of the tee 314 is connected by a tube 316 to the inlet of a flow accelerator cartridge 317. The flow accelerator cartridge 317 is provided with a valve member 318 which is yieldably urged towards a normally closed position by a spring 319 to control the flow of gas from the inlet to the outlet of the flow accelerator cartridge 317. The valve member 318 is provided with a stem 321 carried by a diaphragm 322. A chamber 323 is provided on one side of the diaphragm 322.

Source gas is also supplied from the tee 314 through a tube 326 to a tee 327 mounted in the inlet of the base line control cartridge 328. The base line control cartridge 328 is provided with a valve member 331 movable between open and closed positions to control the flow of gas from the inlet to the outlet. The valve member 331 is provided with a valve stem 332 coupled to a diaphragm 333. The diaphragm 333 is biased in its position by a pair of springs 334 and 336, the bias of which can be adjusted by the use of a control knob 337. The base line control cartridge 328 is provided with a chamber 338 which is provided on one side of the diaphragm 333.

Source gas is also supplied from the tee 327 through a tube 339 to the inlet of the bellows refill cartridge 341. The bellows refill cartridge is provided with a valve member 342 which is movable between open and closed positions and is normally urged towards a closed position by spring 343. The valve member has a stem 344 carried by a diaphragm 346. A chamber 347 is provided on one side of the diaphragm 346.

Source gas is also supplied from the inlet tube 296 through a tube 347 to the inlet of the refill control valve assembly 132. The refill control valve assembly 132 is provided with a valve member 348 which is movable between open and closed positions and which is normally urged towards a closed position by spring 349. The valve member 348 is provided with a valve stem 351 which is adapted to be engaged by the operating lever 131 to move the same from a closed to an open position.

Source gas is also supplied from the tube 296 through a tube 353 to the inlet of an expiratory termination cartridge 354. The expiratory termination cartridge 354 is provided with a valve member 356 movable between open and closed positions and yieldably held in an open position by spring 357. The valve member is provided with a valve stem 358 carried by a diaphragm 359. The expiratory termination cartridge 354 is provided with a chamber 361 on one side of the diaphragm 359.

When the sequencing servo assembly 301 moves to the open position, source gas is supplied from the outlet through a tube 362 to the manifold 363 of a flow rate control valve assembly 364. The valve assembly 364 is provided with a control knob 366 for adjusting the flow of inspiratory gas from the tube 362 to the outlet of the control valve assembly 364 connected to a tube 367. The tube 367 is connected to tee 368. The tee 368 is connected by a tube 369 to a tee 371 and the tee 371 is connected by a tube 372 to the outer jets 373 of a master venturi assembly 376. The venturi assembly 376 is provided with a body 377 which has a venturi-like passage 378. The master venturi assembly 376 has its outlet connected to the outlet of a sensing venturi assembly 379. The sensing venturi assembly 379 is provided with a body 381 which has a venturi-like passage 382 therein. The sensing venturi assembly 379 is mounted upon the inlet of a base line venturi assembly 383 which is provided with a body 384 having a venturi-like passage 386 therein. The base line venturi 383 is connected to the bellows container 112 of the bellows assembly 74. Inspiratory gas is also supplied from the tee 371 through a tube 391 to a chamber 392 of an exhalation valve assembly 393. The exhalation valve assembly 393 is provided with a valve member 394 which is provided with a valve stem 396 carried by a diaphragm 397. The exhalation valve assembly 393 is provided with outlet 398 which is open to the atmosphere. As can be seen from FIG. 4, the valve member 394 controls the flow of gas from the inlet of the base line venturi assembly 383. It can be seen that when the chamber 392 is pressurized the exhalation valve member 394 will be retained in the closed position. A flapper type inlet valve 399 is also provided at the inlet of the base line venturi assembly 383. An inlet filter 401 and inlet flapper valve 402 are carried by the master venturi assembly 376.

To make it possible to provide flow acceleration, the tee 368 is connected by a tube 404 to a tee 406. Tee 406 is connected by tee 407 to a flow acceleration slope control valve assembly 408 which is provided with a control knob 409. The outlet of the flow acceleration slope control valve assembly 408 is connected to a tee 411 which is connected by a tube 412 to the chamber 323 of the flow acceleration cartridge 317. The tee 411 is also connected by a tube 413 to a check valve assembly 414. The check 414 is connected by tube 416 to one leg of the tee 406. The outlet of the flow acceleration cartridge 317 is connected by a tube 416 to the center jet 417 of the master venturi assembly 376.

The inlet of the sensing venturi assembly 379 is connected by a tube 419 to the chamber 307 of the sequencing servo assembly 301.

Inspiratory gases are supplied from the manifold 363 through a tube 421 through a check valve assembly 422. Check valve assembly 422 is connected by a tube 423 to a tee 424. One leg of the tee 424 is connected by a tube 426 to the chamber 361 of the expiratory termination cartridge 354. The other leg of the tee 424 is connected by a tube 427 to the inlet of an expiratory time control valve assembly 428, which is provided with a control knob 429. The control valve assembly 428 is provided with an outlet 431 which is open to the atmosphere. The outlet of the expiratory termination cartridge 354 is connected by a tube 431 to the jet 432 of the sensing venturi assembly 379.

The chamber 338 of the base line control cartridge 328 is connected by a tube 434 to a tee 436, mounted upon a fitting 437 which is in communication with the large breathing tube 102. The tee 436 is connected by a tube 437 to an orifice 438. The orifice 438 is connected by a tube 439 to a pressure manometer 441. The outlet of the base line control cartridge 328 is connected by a tube 442 to the jet 443 of the base line venturi assembly 383.

The outlet of the refill control valve assembly 132 is connected by a tube 446 through a check valve assembly 447 to a tube 448. Tube 448 is connected by tube 449 to a tee 449. One leg of tee 449 is connected by a tube 451 to the chamber 347 of the bellows refill cartridge 341. The other leg of the tee 449 is connected by a tube 452 to a refill time-control valve assembly 453 which is provided with a control knob 454. The refill time-control valve assembly 453 is provided with an outlet 456 which is open to the atmosphere.

The aspirator power socket 312 of the anesthesia respirator 71 is connected by a tube 461 to the aspirator or suction unit 84.

The scavenging fitting 284 is connected to a tube 462 which is adapted to be connected to the scavenging system provided by the hospital or any other suitable connection which can be utilized for evacuating undesired gases. The fitting 284 is also connected by a tube 463 to the scavenging outlet 276 provided on the anesthesia generator 276. It is also connected by a tee (not shown) to a tube 464 of the relief valve assembly 103.

The outlet of the bellows refill cartridge assembly 341 is connected by a tube 466 to a check valve 467. The check valve 467 is connected by a tube 468 to a tee 469. The tee 469 is connected to a tube 461 to the inlet to the bellows 111. The tee 469 is connected by a tube 472 to a check valve 473. The check valve 473 is connected by a tube 473 to the circle flow inlet fitting 282.

The operation of the anesthesia apparatus may now be briefly described as follows. Let it be assumed that the face mask 101 has been placed over the face of the patient and that it is desired to administer an anesthesia gas to the patient. The anesthesiologist can seat himself in the chair 56 and then can proceed with the operation of the control of the anesthesia apparatus. To initiate operation, it may be preferable to pull out the switch over shuttle valve member by operation of the knob 118 so that anesthesia gas will be initially supplied to the bag 82 rather than to the bellows 111. The anesthesia gas will be supplied through the large tube 102 to the patient mask 101 during the time that the bag 82 is being manually compressed. When the patient exhales gas will pass from the face mask 101 through the $CO_2$ absorber 94 and then back into the bag 82. The desired mixture of anesthesia gases is supplied through the blender 321 to the vaporizer 77 and thence to the $CO_2$ absorber 94 through the tube 292. Thus it can be seen that with the present anesthesia apparatus, anesthesia can be supplied to the patient manually.

When it is desired to convert to a controlled or assisted respiration in conjunction with the administration of anesthesia, the knob 118 is operated to push the shuttle valve inwardly which causes the gases to be delivered to the interior of the bellows 111.

Since oxygen is one of the gases being utilized in conjunction with the anesthesia gases being supplied to the patient, oxygen is also utilized for driving the bellows 111. The operation of the respirator 71 for driving the bellows is controlled by the sequencing servo 301 which is provided with the compound adjustment knob 302 to provide the desired inspiratory pressures and to also provide the desired starting effort. The sequencing servo 301 is movable between on and off positions, and when moved to the on position, source gas is supplied from the inlet 183 to the tube 296, tee 297, tube 298, tee 299 through the sequencing servo assembly 301 and then through the tube 362 through the flow control valve assembly 364, tube 367, tee 368, tube 369, tee 371, tube 372 to the outer jets of the master venturi assembly 376 and thence through the base line venturi assembly 383 into the interior of the canister 112. The rate of flow of source gas into the canister 112 is controlled by the adjustment of the flow rate control valve assembly 364. As gas enters the canister 112, the bellows 111 will be raised to cause anesthesia gases to be supplied through the tube 102 to the patient. The length of the inspiratory phase is determined by the time when a predetermined pressure is reached within the container 112. This pressure is sensed in the sensing venturi assembly through the line 419 which is connected to the chamber 307 of the sequencing servo assembly 301. It can be seen that when a predetermined pressure is reached as determined by the adjustment of the compound control knob 302, the valve member 303 will be moved to a closed position to terminate the flow of source gas through the flow rate control valve assembly 364.

During the inspiratory phase, the exhalation valve assembly 393 is maintained in a closed position by source gas being supplied from the tee 371 through the line 391. As soon as the inspiratory phase has been terminated, the exhalation valve is permitted to open and the gas contained within the canister or container 112 is vented to the atmosphere. This permits the patient to exhale and the exhaled gas will again pass through the $CO_2$ absorber 94 and back into the bellows 111 so that the bellows 111 can drop in under the force of gravity in the canister 112.

The length of the exhalation phase is determined by the adjustment of the expiratory time control valve control assembly 428. As can be seen, this valve assembly controls the bleed off of gas from the chamber 361 of the expiratory termination cartridge 354. As soon as there has been a bleed off of sufficient gas, the valve member 356 under the urging of spring 357 is moved to an open position and source gas will flow from the tube 353 through the expiratory termination cartridge 354 through the tube 431 into the jet 437 of the sensing venturi assembly 379. The introduction of gas through the jet 437 will cause a negative pressure condition to be created within the sensing servo venturi assembly 379. This condition will be sensed immediately through the line 419 which is connected to the chamber 307 of the sequencing servo assembly 301 to cause the diaphragm 306 to move the valve member 303 to an open position to terminate the expiratory phase and to initiate another inspiratory phase. Source gas will then be again supplied to the canister 112 to cause raising of the bellows and to supply the anesthesia gases to the patient.

As in conjunction with the manual operation of the bag 82, anesthesia gas as required is supplied to the $CO_2$ absorber 94 through the tube 292.

The anesthesia respirator 71 is provided with additional features which are also advantageous in administering of anesthesia. For example, flow acceleration can be provided for a predetermined interval of time. This interval of time can be adjusted by adjustment of the control knob 409 on the flow acceleration slope control valve assembly 408 to control the bleed in of inspiratory gas from the tube 367 to the chamber 323 of the flow acceleration cartridge 317. As soon as the pressure within the chamber 323 reaches a predetermined pressure, the valve member 318 is moved to an open position against the force of the spring 319 to permit source gas to flow from the tube 319 into the tube 416 to supply additional inspiratory gases through the center jet 417 of the master venturi assembly 376. If still additional gases are required during the inhalation phase, this gas can be supplied from the atmosphere through the inlet filter 401 and through the gate 402. The supply of flow acceleration gases will be terminated at the termination of the inspiratory phase because upon termination of the inspiratory phase, the gas within the chamber 323 will be dumped through the check valve 414 through the master venturi and to the atmosphere through the open exhalation valve assembly 393.

In the event it is desired to cause the patient to exhale against a positive end expiratory pressure, this can be obtained by supplying gas to the base line venturi assembly 383. The base line control assembly 328 has a chamber 338 which is in communication through a tube 434 with the interior of the bellows 111. Thus as soon as the pressure in the bellows 111 drops below a predetermined pressure as for example as soon as exhalation commences, the valve member 331 will be moved to an open position to permit source gas to flow through the line 442 and through the jet 443 into the base line venturi assembly 383 to establish a positive pressure which the gases in the canister 112 must overcome before they can be exhausted through the exhalation valve assembly 393.

When there is insufficient anesthesia gas within the bellows 111 to supply the necessary anesthesia gas to the patient during the inspiratory phase, the operating lever 131 will be struck in the manner hereinbefore described to cause opening of the valve member 348 against the force of spring 349. This will permit source gas to flow from the tube 347 through the refill control valve assembly 132 into the tube 446, check valve 447, tube 448, tee 449, tube 451 into the chamber 347 of the bellows refill cartridge 341. As soon as the chamber 347 is sufficiently pressurized, the valve member 342 will be moved to an open position against the force of the spring 343 to permit source gas in the form of oxygen to be supplied from the tube 339 through the bellows refill cartridge 341 through the tube 466, check valve 468, tube 468, tee 469 and tube 471 into the inlet for the bellows 111. Refilling continues until the pressure in the chamber 347 is bled off through the refill time control valve assembly 453. The rate of bleed off is controlled by the adjustment provided by the knob 454.

In view of the foregoing, it can be seen that anesthesia gases can be administered to the patient in many different ways. Flow acceleration can be provided. In addition assistance or controlling respiration of the patient can be controlled with any desired positive end expiratory pressure through the use of the base line control cartridge 329. In other words, a constant positive pressure can be provided against which the patient must exhale.

The anesthesia apparatus can be readily augmented into an intensive care unit by merely adding an additional respirator such as the respirator disclosed in co-pending application Ser. No. 730,722 filed Oct. 8, 1976. This ventilator can be mounted upon the vertical rod 19. Similarly, if desired, patient breathing monitoring apparatus can also be provided such as of the type disclosed in application Ser. No. 730,841 filed Oct. 8, 1976. This also can be mounted on the support rod 19 in a position close to the respirator so that it can monitor the operation of the respirator. Thus it can be seen that by these simple additions and very little additional tubing, the anesthesia apparatus can be converted into a combination anesthesia and intensive care unit which has many uses.

It can be seen that the combination anesthesia and intensive care unit is mounted upon a stand 12 so that it can be readily shifted from one location to another as for example from the operating room to an intensive care unit in a hospital. The chair assembly 54 which is provided is particularly advantageous when the unit is utilized for administering anesthesia. The chair permits the anesthesiologist to control the operation of the anesthesia apparatus for long operations without fatiguing the anesthesiologist. The stand is provided with many auxiliary devices to aid the anesthesiologist in the operation of the apparatus as hereinbefore described.

The stand is provided with a cabinet which has drawers which are readily accessible to the anesthesiologist and in which equipment can be stored. The stand is also provided with a shelf 31 which can be utilized for carrying equipment which can be utilized in conjunction with the apparatus.

When it is desired to utilize the apparatus as an intensive care unit, the chair assembly 54 can be readily disconnected from the stand 12.

It is apparent from the foregoing, that there has been provided a combination anesthesia and intensive care unit which has many desirable features and which has been designed to minimize as much as possible the fatigue to anesthesiologists particularly during long operations.

What is claimed is:

1. In an anesthesia apparatus having an inhalation phase and an exhalation phase in its operative cycle for supplying anesthesia gases to a patient from a source of anesthesia gas, a controller having an inlet and an outlet with the inlet adapted to be connected to the source of anesthesia gases, the controller having control valve means movable between open and closed positions to control the flow of gases from the inlet to the outlet, said control valve means being in the open position during the inhalation phase and in the closed position during the exhalation phase, the controller having a diaphragm coupled to the control valve member and a chamber formed on the one side of the diaphragm, a canister, a bellows disposed in the canister, a patient adapter, means connecting the interior of the bellows to the patient adapter so that gases can be supplied from the interior of the bellows to the patient adapter and from the patient adapter to the interior of the bellows, means connecting the outlet of the controller to the interior of the canister, an exhalation valve assembly connected to the interior of the canister and having an exhalation valve movable between open and closed positions to control the flow of gases from the canister, means connected to the outlet of the controller and to the exhalation valve assembly for maintaining the exhalation valve assembly in a closed position during the inhalation phase, means connecting the interior of the canister to the chamber of the controller so that when a predetermined pressure is reached within the canister, the control valve member of the controller is moved to a closed position to terminate the inhalation phase and to initiate the exhalation phase, a venturi assembly including a jet disposed between the exhalation valve assembly and the interior of the canister and means for supplying a jet of gases to the venturi assembly during the exhalation phase so that the patient must exhale against a positive pressure.

2. Apparatus as in claim 1 wherein said means for supplying a jet of gases to the venturi assembly includes a control valve assembly having an inlet and an outlet with the inlet connected to the source of gas and having the outlet connected to the jet in the venturi assembly, a valve member movable between open and closed positions to control the flow of gas from the source to the jet in the venturi assembly and diaphragm operated means coupled to the interior of the bellows for moving the last named valve member between open and closed positions.

3. Apparatus as in claim 1 together with flow acceleration means including a flow acceleration cartridge having an inlet and an outlet with the inlet connected to the source of gas and the outlet coupled into the interior of the canister, a valve member movable between open and closed positions for controlling the flow of gas from the inlet to the outlet and diaphragm operated means for controlling the movement of the valve member, said diaphragm operated means including a diaphragm, a chamber disposed on the one side of the diaphragm and means for bleeding gas from the outlet of the controller into the last named chamber.

4. Apparatus as in claim 1 together with means for refilling the interior of the bellows when the bellows contains insufficient gases for the patient during the inhalation phase, said refilling means including a cartridge having an inlet and an outlet with the inlet connected to the source of gas and with the outlet connected into the interior of the bellows, a valve member movable between open and closed positions for controlling the flow of gas from the inlet to the outlet and diaphragm operated means including a diaphragm for controlling movement of the valve member between said open and closed positions and a chamber formed on one side of the diaphragm and means for supplying gas to the last named chamber when insufficient gas is supplied from the interior of the bellows to the patient to cause the valve member to move to an open position to permit additional gas to be supplied from the source to the interior of the bellows and to the patient.

* * * * *